United States Patent [19]

Clemmons

[11] Patent Number: 5,030,555
[45] Date of Patent: Jul. 9, 1991

[54] MEMBRANE-STRIP REAGENT SERODIAGNOSTIC APPARATUS AND METHOD

[75] Inventor: Roger M. Clemmons, Gainesville, Fla.

[73] Assignee: University of Florida, Gainesville, Fla.

[21] Appl. No.: 243,257

[22] Filed: Sep. 12, 1988

[51] Int. Cl.[5] .................. G01N 33/538; G01N 33/545; G01N 33/549; G01N 33/569
[52] U.S. Cl. .......................................... 435/5; 422/56; 422/57; 422/58; 435/7.94; 435/288; 435/299; 435/300; 435/301; 435/311; 435/805; 435/810; 436/177; 436/178; 436/518; 436/528; 436/530; 436/531; 436/535; 436/808; 436/810; 436/811; 436/813; 436/820
[58] Field of Search .................. 435/7, 288, 292, 293, 435/294, 299, 300, 301, 311, 805, 810, 5; 436/518, 524, 528, 531, 532, 807, 808, 810, 824, 530, 535, 177, 178, 811, 813, 820; 422/56, 57, 58, 60

[56] References Cited

U.S. PATENT DOCUMENTS

| | | |
|---|---|---|
| 2,370,683 | 3/1945 | Palma . |
| 3,962,413 | 6/1976 | George et al. . |
| 4,078,892 | 3/1978 | Steinbrink, Jr. . |
| 4,246,339 | 1/1981 | Cole ................... 436/808 X |
| 4,305,721 | 12/1981 | Bernstein . |
| 4,376,110 | 3/1983 | David et al. ............ 436/513 |
| 4,446,232 | 5/1984 | Liotta ..................... 435/7 |
| 4,459,358 | 7/1984 | Berke ............... 436/810 X |
| 4,515,889 | 5/1985 | Klose ..................... 435/4 |
| 4,520,113 | 5/1985 | Gallo et al. ............ 436/504 |
| 4,592,994 | 6/1986 | Mattiasson ............. 435/7 |
| 4,632,901 | 12/1986 | Valkirs .................. 435/7 X |
| 4,677,058 | 6/1987 | Tryggvason et al. ....... 435/7 |
| 4,693,985 | 9/1987 | Degen et al. ............ 436/531 |
| 4,716,104 | 12/1987 | Harris et al. ............ 435/5 |
| 4,727,037 | 2/1988 | Ring ...................... 436/548 |
| 4,803,170 | 2/1989 | Stanton et al. ........... 422/56 |
| 4,818,677 | 4/1989 | Hay-Kaufman ........ 436/810 X |
| 4,826,759 | 5/1989 | Guire ................... 436/810 X |
| 4,859,583 | 8/1989 | Heller .................. 436/810 X |

FOREIGN PATENT DOCUMENTS 8202211 7/1982 World Int. Prop. O. .......... 436/807

OTHER PUBLICATIONS

Patel et al., Clin. Chem., vol. 32 (1986), pp. 1832-1835.
Voller et al.,-Enzyme-Linked Immunosorbent Assay, in Manual of Clinical Laboratory Immunology, Chapter 17, pp. 99-109.
Marlow et al.,-Journal of Immunological Methods, vol. 101, pp. 133-139 (1987).
Towbin et al.,-Journal of Immunological Methods, vol. 72, pp. 313-346 (1984).

Primary Examiner—Christine Nucker
Attorney, Agent, or Firm—Foley & Lardner, Schwartz, Jeffery, Schwaab, Mack, Blumenthal & Evans

[57] ABSTRACT

For the serodiagnosis of a fluid sample, it is particularly advantageous to use a device comprising (A) a supported, porous membrane wherein a first immunoreagent is bound so as to be capable of binding a foreign analyte and forming a complex when the foreign analyte is brought into contact therewith; and (B) a matrix which presents a first surface and an opposing second surface and which contains a second, labeled immunoreagent that is capable of binding the foreign analyte to form a labeled complex when the foreign analyte is sandwiched between the first immunoreagent and the second immunoreagent. In such a device, the first surface of the matrix is adjacent to a surface of the membrane, (ii) the matrix is wettable by or soluble in an aqueous fluid, and (iii) the second immunoreagent is mobilized when the matrix is wetted.

20 Claims, 4 Drawing Sheets

MEMBRANE-STRIP REAGENT SERODIAGNOSTIC APPARATUS AND METHOD

FIELD OF THE INVENTION

This invention relates to an apparatus and method for detecting the presence of antigens and/or antibodies in biological fluids.

BACKGROUND OF THE INVENTION

It is known to use immunodiagnostic procedures for the detection of antigens and antibodies in biological fluids. Such procedures have been developed for hormones, infectious agents, serum antibodies, pharmaceutical products, and drugs of abuse, to name a few. One procedure, enzyme-linked immunosorbent assay, or ELISA as it is sometimes called, has assumed a dominant role in diagnostic laboratories due to its relative sensitivity and specificity, while at the same time avoiding the need for extremely sophisticated equipment and radioactive materials. In the heterogeneous ELIZA procedure, an immunoreagent is immobilized on a carrier surface. The immunoreagent is capable of binding or reacting with the target material for which testing is being done. Following contact with the fluid suspected of containing the target material, a second, enzyme-conjugated reagent, incubated with the bound immunoreagent and washed to remove any unbound enzyme-conjugated immunoreagent. A substrate is then added which will develop a color reaction in the presence of the enzyme-conjugated immunoreagent. In a typical ELISA technique, a monoclonal antibody against a specific protein is absorbed to the surface of a plastic, e.g. polystyrene, microtiter plate well. The remaining surface binding sites are blocked, usually with glycine, avidin, or the like, to prevent nonspecific interaction at the surface of the plastic. The specific protein is then allowed to interact and bind to the monoclonal antibody by placing a fluid containing or suspected of containing the same in contact with the plastic surface. The surface is then washed to remove unbound protein. Enzyme-conjugated antibody is then added to the well and allowed to bind to the previously bound specific protein. The enzyme-conjugated antibody may be monoclonal, against the same or another epitope of the specific protein, or polyclonal against a number of epitopes of the specific protein. The microtiter well is then washed free of the unbound enzyme-conjugated antibody. A substrate capable of producing a detectable end product in the presence of the enzyme system is then added to the well and incubated. The presence of the end product is estimated visually or photometrically.

While the ELISA technique is advantageous in many respects as noted above, there remain numerous problems involved with its application. The immobilized antibody is typically bound to a bead or small particle, or coated on the surface of a microtiter plate well. This requires substantial incubation periods for each step in the procedure and considerable washing between steps. As a result, ELISA can be time-consuming. Even when several samples are run simultaneously, the procedure can require several hours to conduct the assay. In addition, there is a strict protocol for ELISA, particularly with respect to the timing of the incubation steps, and measuring of reagents, tending to limit the use of ELISA to large hospitals and clinical reference laboratories.

From U.S. Pat. No. 4,376,110, it is known to employ two-site immunometric assays using pairs of monoclonal antibodies, one bound to a solid phase, such as beads, and the other labeled in a solution phase to permit detection. The monoclonal antibody pairs recognize different epitopic sites on an antigen and obviate an intermediate washing step.

It is known from U.S. Pat. No. 4,446,232 to use a two-zoned device having bound antigens for enzyme-imunoassaying procedures. In this device, a top layer contains antibodies which react with antigens passing therethrough. A second layer contains immobilized antigens which will react with and adhere to, and thus immobilize, antibodies which have not reacted with the antigens in the first layer. A third layer containing a reactive substrate is positioned beneath the second layer and serves to detect through a color-forming reaction the antibody-antigen sandwiches which pass through the second or intermediate layer.

It is known from U.S. Pat. No. 4,632,901 to employ an apparatus including an immunoreagent-binding membrane adjacent to an absorbent material in conducting ELISA procedures. The absorbent material has capillaries formed by the orientation of fibers transversely to the membrane surface to draw immunoreagents, washing solutions and reactive substrates through the membrane.

ELISA procedures are described in detail in Voller et al., *Manual of Clinical Laboratory Immunology*, Chapter 17, pp. 99–109. Immunoblotting and slot-blot assay procedures using a membrane which covalently binds proteins are described in Towbin, *Journal of Immunological Methods*, Vol. 72, pp. 313–346 (1984); and Marlow et al., *Journal of Immunological Methods*, Vol. 101, pp. 133–139 (1987).

A method for the serological detection of antibodies to HTLV-III in sera of patients with AIDS and pre-AIDS conditions is described in U.S. Pat. No. 4,520,113.

Other references which describe assaying procedures include U.S. Pat. Nos. 3,962,413; 4,305,721; 2,370,683; and 4,078,892.

SUMMARY OF THE INVENTION

The present invention provides a serodiagnostic device which facilitates an ELISA-type procedure. The invention also provides a novel serodiagnostic method.

In one aspect the invention provides a serodiagnostic device which includes a membrane having first and second opposite sides. The membrane is porous and capable of binding immunoreagents. An immunoreagent is bound to the membrane adjacent one side thereof. Means are provided in fluid communication with the first membrane side for introducing a fluid sample thereto. Means are provided in fluid communication with the second membrane side for drawing fluid through the membrane and for collecting the drawn fluid. An antigen-antibody reaction is obtained between the membrane-bound immunoreagent and any substance in the sample which is reactive or forms a complex therewith. The introduction means the membrane and the drawing and collecting means are unitized, are self-contained, to inhibit or prevent escape of fluids introduced and collected in the device so that the entire device may be disposable following the diagnostic procedure. The collecting means has sufficient volume to collect, for example, the sample, additional reagent solutions, and any intermediate washes. The volume of the collecting means is preferably sufficient to collect the sample, a wash introduced onto the membrane following the sample introduction, a subsequent labeled immunoreagent solution introduced onto the membrane to react with the antigen-antibody complex formed by the sample and the membrane-bound immunoreagent, another wash introduced onto the membrane to separate any uncomplexed or unreacted labeled immunoreagent from the membrane, a substrate solution introduced onto the membrane to react with the labeled immunoreagent-antigen-antibody complex bound to the membrane, and another wash to separate the substrate from the membrane. The device preferably further includes means for visualizing or otherwise detecting a color-forming reaction product bound to the membrane, such as a transparent panel or window, indicative of the presence of a substance in the sample reactive with the membrane-bound immunoreagent and the labeled immunoreagent.

The invention also provides a method for conducting a serodiagnostic analysis of a sample for the presence of a specific substance or substances therein. The method includes the steps of: (a) drawing a sample fluid into a serodiagnostic device which has a membrane with first and second opposite sides, wherein the membrane is porous and has an immunoreagent bound thereto; (b) incubating the sample adjacent the membrane to obtain an antigen-antibody reaction between the membrane-bound immunoreagent and any substance in the sample which forms a complex therewith; (c) drawing washing solution through said membrane to rinse said membrane essentially free of the sample fluid; (d) drawing a labeled immunoreagent solution through the membrane to complex with the membrane-bound antigen-antibody complex; (e) drawing washing solution through the membrane to rinse the membrane essentially free of the uncomplexed labeled immunoreagent; (f) drawing a substrate reactive with said membrane-bound labeled immuoreagent-antigen-antibody reaction product through the membrane to obtain a visually observable or otherwise detectable reaction product on the membrane; and (g) collecting the sample, washing solution and labeled immunoreagent solution and substrate in the device. The device is preferably self-contained so that the operator is not exposed to any of the sample and/or reagents during the test procedure, and the device may be disposed of following completion of the test procedure.

In another aspect, the invention provides a serodiagnostic device which includes a porous membrane and a matrix. The porous membrane has an immunoreagent absorbed thereon, a first surface for receiving a fluid sample in contact therewith, and a second surface opposite the first surface. An antigen-antibody reaction is obtained between the membrane-bound immunoreagent and any substance in the sample which forms a complex or is otherwise reactive therewith. The matrix is adjacent the second surface of the membrane and contains a labeled immunoreagent to complex with the membrane-bound antigen-antibody complex. The labeled immunoreagent is mobilizable by fluid passing through the membrane from the first side to the second side. The mobilized labeled immunoreagent is capable of complexing with the membrane-bound antigen-antibody complex to obtain a detectable labeled immunoreagent antigen-antibody complex bound to the membrane. Unreacted labeled immunoreagent adjacent the membrane is further separable therefrom by the fluid to facilitate visual or other detection of a detectable reaction product of a substrate permeable through the membrane and reactive with the labeled immunoreagent to form the reaction product.

There is also provided a method for serodiagnosis of a fluid sample. The method includes the step of contacting a porous membrane with the sample. The porous membrane has an immunoreagent absorbed thereon, a first surface for receiving the fluid sample in contact therewith, a second surface opposite the first surface, and a matrix adjacent the second surface of the membrane. The porous membrane has an immunoreagent to obtain an antigen-antibody reaction product between the immunoreagent and any substance in the sample which is reactive therewith. The matrix contains a labeled immunoreagent reactive with the antigen-antibody reaction product. The labeled immunoreagent is mobilized in the matrix by fluid passing through the membrane from the first side to the second side. The method also includes the steps of rinsing the membrane to remove unreacted labeled immunoreagent from adjacent the membrane, contacting the membrane with a substrate solution reactive with the membrane-bound labeled immunoreagent-antigen-antibody reaction product, and detecting the reaction product of the substrate and the labeled immunoreagent indicative of a positive test for the presence of a reactive substance in the sample.

DETAILED DESCRIPTIONS OF THE PREFERRED EMBODIMENTS

Figure 5:
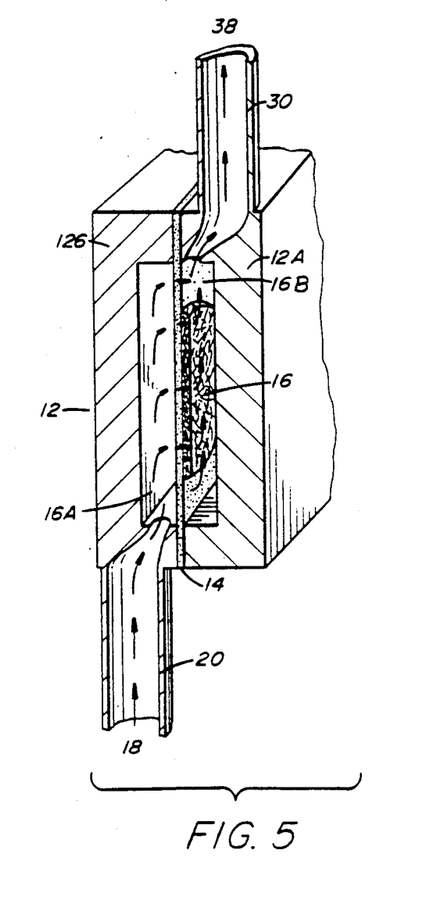
FIG. 5 is an enlarged cross-sectional view of the chamber of the device of FIG. 1 depicted in schematic form.
Figure 6:
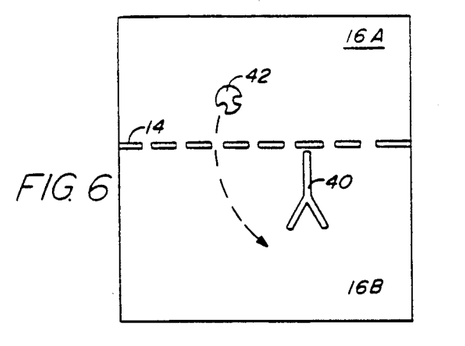
FIG. 6 is a diagrammatical illustration of antigen-antibody complexing in the device of FIG. 1.
Figure 7:
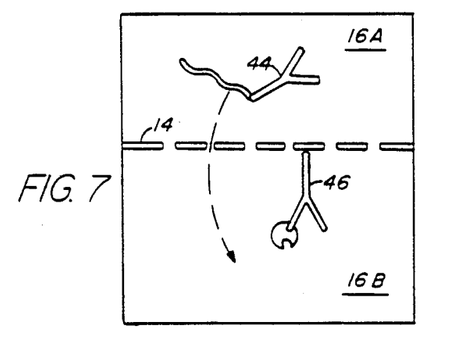
FIG. 7 is a diagrammatical illustration of the labeled immunoreagent-antigen-antibody complexing in the device of FIG. 1.
Figure 8:
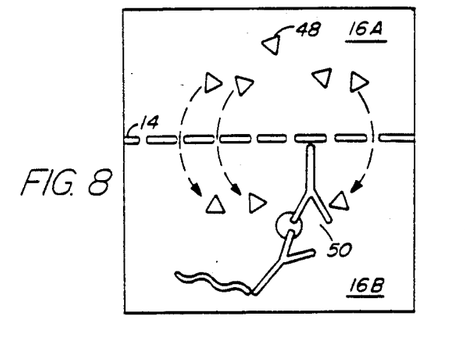
FIG. 8 is a diagrammatical illustration of the reaction between a substrate and labeled immunoreagent-antigen-antibody complex in the device of FIG. 1.
Figure 9:
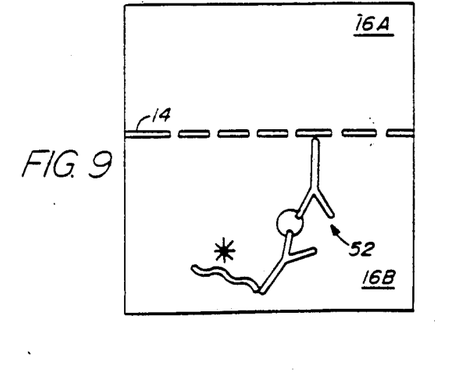
FIG. 9 is a diagrammatical illustration of visual observation for the presence of a suspect material in the device of FIG. 1.
Figure 10:
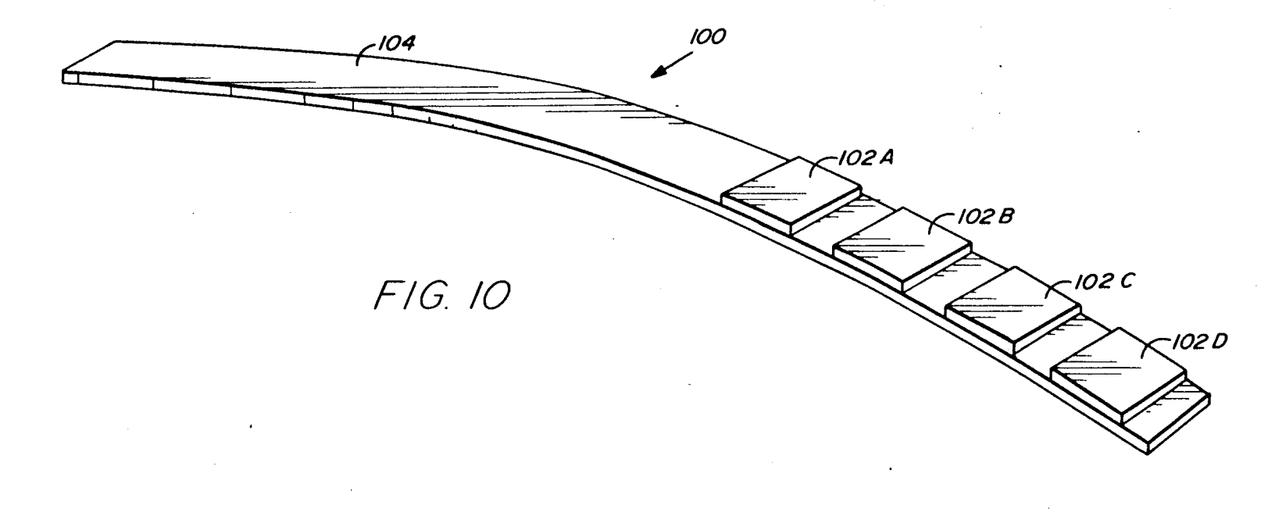
FIG. 10 is a perspective view of an alternate embodiment of a serodiagnostic device according to the present invention.

With reference to FIGS. 1-5, one embodiment of the present invention is a syringe-like device which is adapted to function as a serodiagnostic tool. The device 10 includes cartridge 12 comprising halves 12a and 12b which are assembled together on either side of membrane 14 to form chamber 16 as best seen in FIG. 5. The membrane 14 is thus positioned in the cartridge 12 to divide the chamber 16 into two portions, 16a and 16b. The chamber portion 16a is in fluid communication with inlet means 18 which includes tube 20, needle 22 depending therefrom, needle shield 24 affixed to tube 20 and removable cap or closure 26 which fits into one end of needle shield 24. The tube 20 terminates in needle 22 to provide a means for introducing fluid therethrough into chamber 16 by removing the cap 26 and puncturing or otherwise piercing a septum or another barrier to a source of the fluid to be sampled, or simply immersing the end of the needle 22 in the fluid sample. The shield 24 may be formed of a relatively rigid and preferably clear material to inhibit accidental contact with the needle 22, particularly after it has been introduced to the sample source. This serves to protect the operator of the device 10 from inadvertent exposure to and infection by the sample material.

Figure 1:
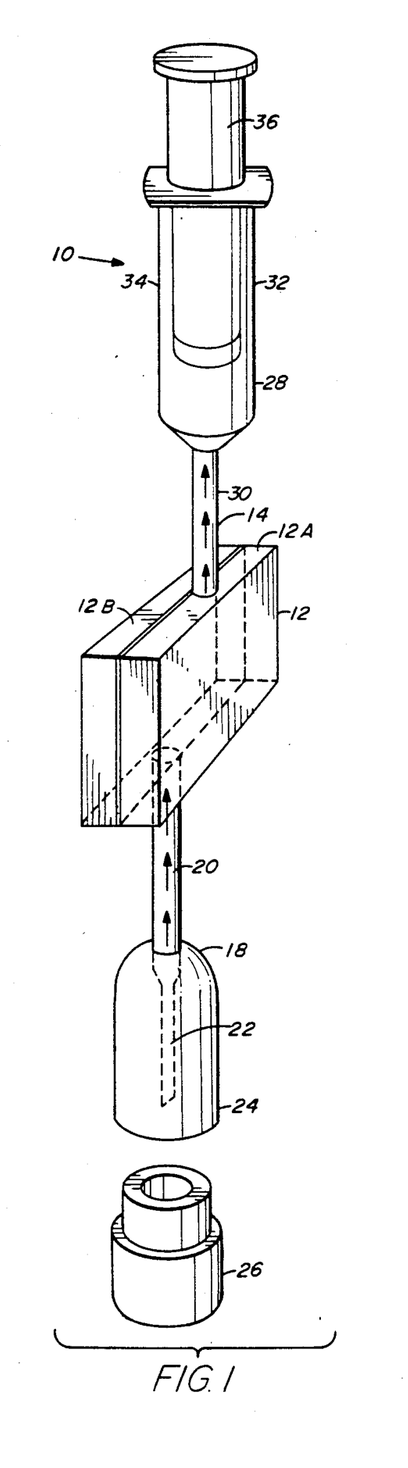
FIG. 1 is a perspective view of a serodiagnostic device according to an embodiment of the present invention.
Figure 2:
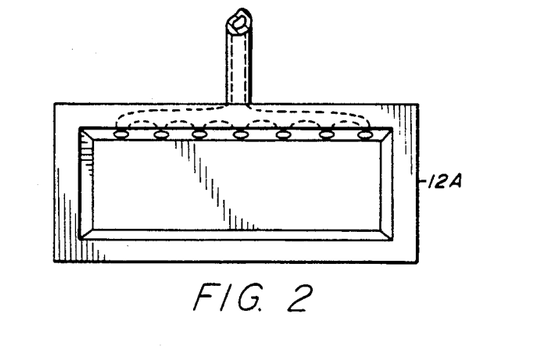
FIG. 2 is a perspective view of a portion of a membrane cartridge from the device of FIG. 1.
Figure 3:
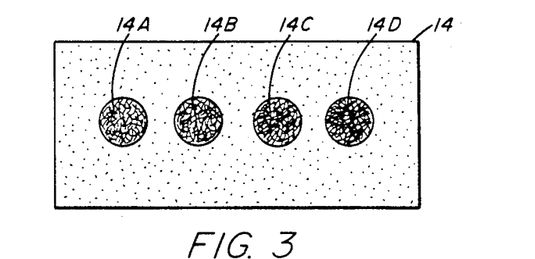
FIG. 3 is an illustration of a membrane placed in the cartridge of the device of FIG. 1.
Figure 4:
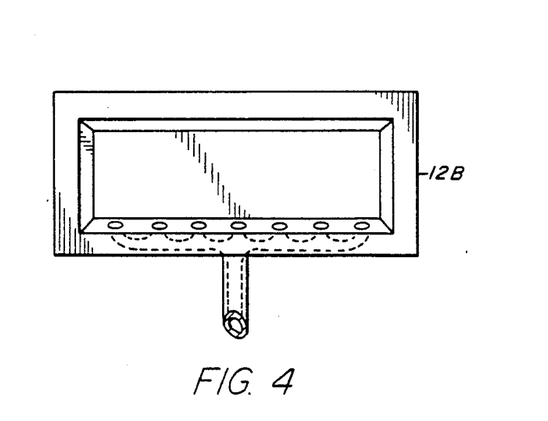
FIG. 4 is a perspective view of another portion of the membrane cartridge of the device of FIG. 1.

The chamber portion 16b is in fluid communication with the fluid drawing/collection means 28 which includes tube 30 and syringe 32. The syringe 32 includes cylindrical housing 34 and piston or plunger 36. In a preferred embodiment, the syringe 32 may include a stop means (not shown) for preventing removal of the plunger 36, as this should otherwise result in potential exposure of the operator of the device 10 to the sample and/or the immunoreagents collected therein. Similarly, a check valve, e.g., of the ball or wafer type (not shown) may be positioned in either the introduction means 18 or in the drawing/collection means 28 (e.g., in the line 20 or 30, respectively). This further serves to minimize the risk of exposure of the operator of the device 10 to the sample and/or immunoreagents by inhibiting accidental discharge of fluid therefrom.

The membrane 14 is made of a porous material which is capable of permitting the transfer of fluid from the sample from the chamber portion 16a into the chamber portion 16b under the effect of the vacuum created by the withdrawal means 28. Generally, a pore size of 0.45 to 3 microns is sufficient for this purpose, with an approximately 1-micron pore size generally being optimal. The pore size should not be too small in order that target particles, such as antigens or antibodies in whole blood or another fluid containing such target particles, will not pass through the membrane 14. The membrane 14 should also be capable of binding proteins, such as antibodies and/or antigen substances. Suitable materials include, for example, nitrocellulose, polyamide, polycarbonate, IMMUNODYNE IMMUNOAFFINITY, and the like.

The cartridge 12 should be constructed of a transparent material, or with a window or other means, to permit detection of labeled immune complexes on the membrane 14 by, for example, visual observation of any color changes that might occur in the membrane 14 during the procedure with the device 10. The design illustrated in FIGS. 1-4 is merely illustrative of one arrangement to permit said detection, and it is contemplated that the cartridge 12 may also be, for example, formed integral with the syringe 32 with the membrane positioned transversely to the longitudinal axis thereof so that it can be viewed from the side or positioned adjacent the syringe 32 in a side-by-side fashion. If desired, a transparent panel may be provided in the cartridge to facilitate viewing of the membrane 14 test sites, with or without magnifying means such as prisms or Fresnel lenses.

Generally, only one side of the membrane 14 must necessarily be visible or otherwise accessible for reading of the results. This is because the bound immunoreagent will usually be bound at one side or the other of the membrane 14, depending on which side thereof is initially treated with the immunoreagent solution.

As shown in FIG. 5, it is preferable to have membrane 14 facing the downstream chamber portion 16b to avoid the possibility that solid filtrate deposited on the 16a side of the membrane 14 from the fluid sample may otherwise impair formation or detection of the antigen-antibody complex. It is likewise preferred to employ an opaque material for the membrane 14 to minimize any difficulty in reading which might result from a solid filtrate being visible through a clear or transparent material employed for the membrane 14, but it is also possible to employ a transparent membrane material, particularly where the fluid sample contains only minor amounts of solid filtrate.

A method according to the present invention in which the tool 10 is employed is illustrated in FIGS. 5-9. In this method, an immunoreagent (e.g., an antibody or an antigen) is bound to the membrane 14 on at least a portion thereof according to conventional techniques for binding an antibody and/or an antigen well known in the art. If desired, several sections of the membrane 14 may be employed for testing for the presence of various different materials and/or for indicating erroneous test procedures.

In the first step of the method, the sample fluid is introduced into the chamber 16 by puncturing a barrier to a source of the sample fluid with needle 22, or otherwise placing needle 22 in the fluid sample, and withdrawing the syringe 36 to draw a portion of the sample fluid into the chamber portion 16a. Fluid entering the chamber portion 16a is subsequently drawn into the chamber portion 16b across the membrane 14 by the vacuum exerted by the fluid-drawing means 28. Material contained within the sample which is in excess of the pore size of the membrane 14 is trapped on the membrane 14 as a solid filtrate and not permitted to pass from chamber portion 16a to chamber portion 16b. The antibody, or other immunoreagent, is preferably bound to one side of the membrane 14 adjacent the downstream chamber portion 16b. As fluid from the sample passes through the membrane 14, any antigen, or other substance reactive with the immunoreagent bound to the membrane 14, reacts with the antibody 40 as illustrated with FIGS. 6-7.

In the second step of the procedure, a washing or flushing solution is drawn through the chamber 16 to rinse away any unreacted fluid from the sample passing through the membrane 14. This is done by positioning the needle 22 in a washing solution and additional retraction of the plunger 36 from the cylinder 34 of the syringe 32. Next, the needle 22 is inserted into a solution containing a labeled antibody 44, or other labeled immunoreagent, which is drawn into the chamber 16 and passed through the membrane 14 to react with the antigen-antibody complex 46 bound to the membrane material 14 in the preceding step.

The washing solution is then generally employed as before to rinse or separate the unreacted labeled immunoreagent 44 from the membrane 14 which, like the previous wash solution, is collected in the chamber 34 of the syringe 32. A substrate is then drawn into the chamber 16 in a similar fashion, and then rinsed again as desired. The substrate 48 or another substance or system is reactive with the labeled immunoreagent-antigen-antibody complex 50 which is bound to the protein 14. The labeled immunoreagent or antibody 44 may be, for example, an antibody reactive with the antigen 42 which is labeled with an enzyme such as peroxidase, alkaline phosphatase or the like. An enzyme system such as DAB-peroxidase or TMB-alkaline phosphatase is preferred so that the resulting complex 52 can be observed by visual observation, such a system generally forming a colored product which can be visualized through the cartridge 12.

A particularly preferred embodiment of the diagnostic device 10, and the corresponding method for use thereof, resides in its adaptation for use in detection of AIDS-associated substances in blood, particularly in fluid samples from donor blood containers. In this embodiment, the membrane 14 contains four reading areas 14a, 14b, 14c and 14d (see FIG. 3) for the presence of HIV antibody, for the presence of HIV-associated antigen such as p24 antigen, for indication of a positive control, and for indication of a negative control, respectively. The membrane area 14a contains bound HIV antigen, preferably p24 antigen. The area 14b contains antibody against HIV-associated antigen, preferably anti-p24 antibody, and especially polyclonal antibody. The area 14c contains enzyme-conjugated or otherwise detectable antibody as an indication for a positive control. The area 14d is blocked against protein binding for a negative control.

In this manner, the device 10 can be used to test for the presence of both AIDS antibody and AIDS antigen in a blood sample, for example, in donor blood. The blood need not be centrifuged as the larger molecular constituents thereof will be filtered out as the fluid passes through the membrane 14. This eliminates centrifuging or gravity settling or other forms of treatment in which the blood plasma must be separated from the whole blood prior to running the AIDS evaluation. Since the detectable immunoreagent complex is formed on the side opposite that on which the filtrate is collected on the membrane 14, there is no interference with the reading of the test result. In addition, the blood can be obtained directly from a donor bag, and the operator is protected from exposure by the needle 22 and its surrounding shield 24.

The labeled immunoreagent solution used to develop the membrane 14 in this preferred embodiment following passage of the blood fluid through the membrane 14 includes two enzyme-conjugated or otherwise detectable antibodies, each of which is selectively reactive each antibody-antigen complex bound to the membrane 14 in the membrane areas 14a and 14b. The first labeled antibody is reactive with the antigen-antibody complex bound in area 14a of the membrane 14 and should be an antibody against the antigen complexed with the membrane-bound antibody of area 14a. The first antibody is preferably derived from a non-human source, such as mouse, equine, goat, rabbit or the like. The second labeled antibody is reactive with the antigen-antibody complex bound in area 14b of the membrane 14, and likewise should be an antibody against the antibody complexed with the membrane-bound antigen of area 14b. The first and second labeled antibodies may be polyclonal or monoclonal antibodies, but preferably are polyclonal antibodies, particularly in the case of the first labeled antibody.

The first and second labeled antibodies in this particular preferred embodiment may be contacted with the membrane 14 sequentially, with an intermediate wash drawn into the device 10 between the first and second labeled antibody solutions. Alternatively and preferably, the first and second labeled antibodies are contained in the same solution to avoid and eliminate the intermediate wash and the subsequent contact with one of the antibodies. In this embodiment, cross-reactivity between the first and second antibodies should be avoided, as well as cross-reactivity of the first labeled antibody with the membrane area 14b antigen, and the second labeled antibody with the membrane area 14a antibody. This can be accomplished by using a modified antigen bound to the membrane area 14b. The modified antigen is obtained by enzymatically fragmenting an antigen source, such as, for example, the p24 protein. With a proteolytic enzyme and collecting fractions obtained by electropheresis and/or gel chromatography, for example. The various fractions of the p24 protein are then used to develop monoclonal or polyclonal antibodies which are specific against the particular p24 fraction, e.g. by immunizing a rodent or another species and collecting the serum and/or developing a hyperdoma clone. These antibodies are then used for enzyme conjugation to obtain the labeled immunoreagent for the membrane area 14a antigen-antibody complex bound to the membrane 14. Another protein fraction from the p24 fractionation is then employed at the antigen which is bound to the membrane area 14b. The membrane area 14b bound antigen should be selectively nonreactive with the labeled immunoreagent used to react with the membrane area 14a antigen-antibody complex. In this manner, cross-reactivity between the membrane area 14a labeled immunoreagent and the membrane area 14b bound antigen is avoided, and thus, the first and second antibodies can be applied to the membrane 14 in the same labeled immunoreagent solution to eliminate the intermediate washing steps and a second treatment with a labeled immunoreagent solution.

An alternate embodiment of the invention is illustrated in FIGS. 10-15. Serodiagnostic device 100 is a "dip-stick" type device on which is located a plurality of test pads, 102a, 102b, 102c and 102d. Each test pad 102a-d is secured to a backing strip 104 which is made of an inert, preferably impermeable, material, such as a plastic such as polyethylene, polypropylene, polystyrene, etc., or paper, coated paper, or the like.

Figure 11:
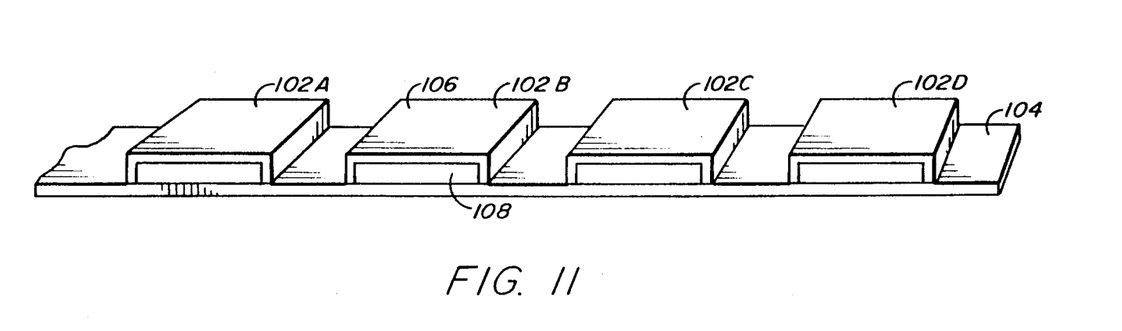
FIG. 11 is an enlarged view of a portion of the device of FIG. 10.
Figure 12:
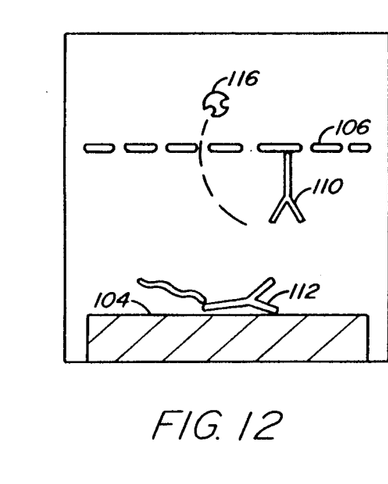
FIG. 12 is a diagrammatical illustration of antigen-antibody complexing and labeled immunoreagent mobilization in the device of FIGS. 10-11.

Each test pad 102a-d includes a porous membrane 106 attached to the support member 104 around the periphery thereof. A matrix 108 is positioned between the membrane 106 and the support member material 104.

One or more of the test pads 102a-d has an antibody absorbed thereon, preferably on a side of the membrane 106 which is adjacent to matrix 108. Instead of antibody 110, it is also contemplated that another immunoreagent, such as, for example, an antigenic substance, may be bound to the membrane 106. The matrix 108 contains unbound labeled antibody 112 or other labeled immunoreagent. The matrix 108 is preferably a wettable or hygroscopic material, and may be an insoluble material, such as cotton, glass, or the like, capable of retaining labeled antibody 112, without binding, or alternatively the matrix material 108 may comprise a soluble material, such as, for example, glycine, sugar, salt, or the like, in which the antibody 112 is dispersed.

The labeled antibody 112 is reactive with a substrate 114 to obtain a detectable reaction product, preferably a colored precipitate. When a colored precipitate reaction product is formed, the test result may be determined by visual observation of the presence of color on the appropriate test pad 102. The membrane 106 may be transparent to facilitate this visual observation. Alternatively, a transparent support material 104 may be employed where the matrix material 108 is soluble and/or matrix 108 is transparent so that the test pad 102 may be observed visually through the support material 104 and/or matrix 108.

Figure 13:
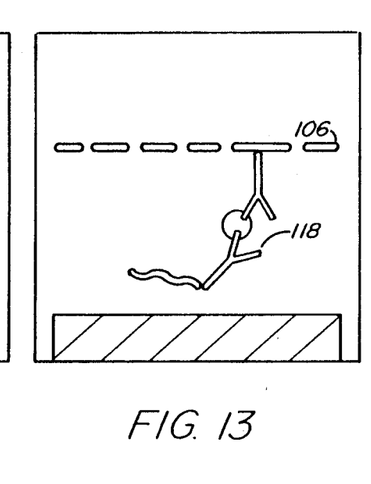
FIG. 13 is a diagrammatical illustration of the labeled immunoreagent-antigen-antibody complex obtained in the device of FIGS. 11-12.
Figure 14:
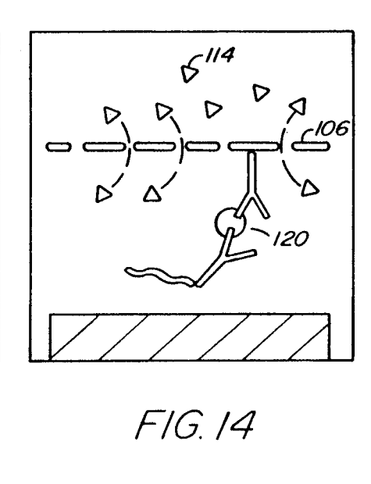
FIG. 14 is a diagrammatical illustration of permeation of the membrane of the device of FIGS. 10-11 by a substrate reactive with the labeled immunoreagent-antigen-antibody complex.
Figure 15:
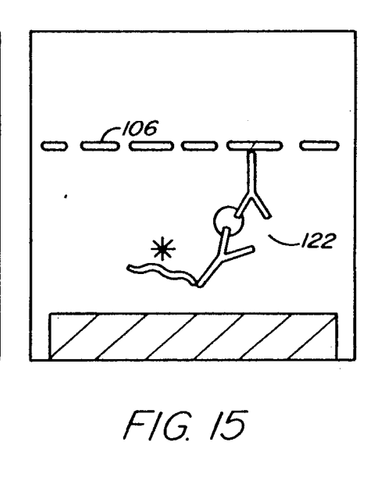
FIG. 15 is a diagrammatical illustration of a visualized test result in the device of FIGS. 10-11.

In the method of the invention employing the "dipstick" device 100, the dip-stick 100 is generally used in a dry form and inserted into a test fluid to be sampled. The sample fluid enters through the membrane 106 into the matrix 108. Any antigen 116 is permitted to react with antibody 110 bound to membrane 106. In this step, the fluid entering the matrix 108 also serves to mobilize the labeled antibody 112 or other immunoreagent which is also reactive with the antigen 116 to form the labeled immunoreagent-antigen-antibody sandwich 118 as illustrated in FIG. 13. The dip-stick is then inserted in a washing solution to remove any unreacted or uncomplexed labeled antibody 112. Following removal of the labeled antibody 118 from the matrix 108 by the rinsing solution, the dip-stick is inserted in a solution of substrate which is reactive with the labeled antibody 112 or other immunoreagent, and also with the labeled antibody-antigen-antibody 120 which is bound to the membrane 106. Following reaction between the substrate 114 and the complex 120, the resulting reaction product 122 (FIG. 15) can be observed as described above.

In a preferred embodiment, the device 100 is used in an AIDS detection device, for example, in human urine specimens. The test pads 102a–d in the device 100 are configured as in the membrane areas 14a–d discussed above in connection with the device 10, with the respective labeled immunoreagents located in the appropriate matrix 108.

In another preferred embodiment, device 100 is packaged to facilitate its use. The package containing the device 100 comprises a sealed container having first and second compartments. The device 100 is placed in one such compartment, and the substrate indicating solution is placed in the other. The compartments may be side-by-side in configuration, or end-to-end, as in a long cigar-type of tube configuration. The end of the device 100 distal the test pad 102 is preferably affixed to a lid for the first compartment. In this manner the test strip is maintained in a sealed condition in the first compartment of the container. When it is desired to employ the device 100, it is removed from the container and placed in the fluid specimen to be tested. If desired, the compartment in which the device 100 is stored before use may also serve as the compartment for receiving the test fluid, for example, urine, serum, or the like. In this manner, the device 100 may be conveniently exposed to the test fluid by inserting the device 100 back into the compartment containing the fluid specimen, sealing it with the lid to which the device 100 is affixed, and shaking or agitating or otherwise incubating the specimen in contact with the device 100. After sufficient contact between the specimen and the device 100, it is removed, rinsed, as desired or appropriate, and placed in the substrate indicator solution in the second compartment. The substrate indicator solution may be placed in contact with the device 100 by removing a lid or other removable enclosure for sealing the substrate indicator solution compartment, and replacing the lid to which the device 100 is affixed in its place. Alternatively, the substrate indictor solution from the second compartment in the container may be placed in another suitable container for contact with the device 100. Following contact between the device 100 and the substrate indicator solution, the device 100 is rinsed as appropriate and read for the presence or absence of the target substance. Where additional washes and/or reagents are required, additional compartments may be provided in the container.

The invention is illustrated by way of the examples which follow:

EXAMPLE 1

A membrane suitable for use in the device illustrated in FIGS. 1–9 was employed to determine the presence of human choriogonadotropin (hCG). A mouse-derived monoclonal antibody against hCG (obtained from Chemicon) was covalently bound to an approximately 3 mm diameter spot on a nylon membrane (pore size 0.65 micron; BioRad Zeta probe) by wetting the membrane with 200 microliters of 0.15M PBS containing 1 microgram of the antibody and drying under vacuum at room temperature. Another membrane spot was bound with a polyclonal-alkaline phosphatase enzyme conjugated rabbit-derived antibody against hCG (Chemicon) as a positive control. A final spot on the membrane was treated with blocking solution (PBS containing 0.05 volume percent TWEEN 20 and 0.19 M glycine) as a negative control. The entire membrane was then treated with PBS at pH 7.4 containing 0.05 percent TWEEN 20 and 0.19 M glycine and allowed to dry at room temperature. The membrane was then cut to a 25 mm diameter and placed in a Gelman syringe filter holder. The membrane was wetted with PBS containing 0.05 vol/vol percent TWEEN 20 by drawing a small portion of the solution through the filter holder using a syringe. A 1 ml sample containing hCG was aspirated through the membrane. The membrane was then washed with 1 ml of PBS-TWEEN, and 1 ml of the enzyme-conjugated antibody was aspirated through the membrane. The membrane was washed with 1 ml of barbital buffer at pH 9.6, and then the color developed using nitroblue tetrazolium. The procedure was repeated with various concentrations of hCG (from 0 to 2500 mIU/ml concentrations) in the samples. A black dot was visible at all positive controls at all hCG concentrations and at all sample membrane locations for hCG concentrations greater than 25 mIU/ml. The background of the membrane (false negative) remained free of any color development. Similar results were also obtained when a nitrocellulose membrane (BioRad; 0.45 micron) was used.

EXAMPLE 2

The procedure of Example 1 was used to test for human hepatitis B surface antigen. A mouse-derived monoclonal against hepatitis B surface antigen (ad/ay) (obtained from Chemicon) was bound to the surface of the membrane and inserted in the filter holder as in Example 1. Following contact with the sample solution containing various concentrations of human hepatitis B surface antigen (ad/ay) (Alpha-Therapeutics), the membrane was contacted with equine-derived polyclonal antibody against hepatitis B surface antigen (ad/ay) (Chemicon) which had been conjugated with a peroxidase enzyme system by the one-step glutaraldehyde method. The membrane was then aspirated with 3,3'-diaminobenzidine (DAB) (3 mg in 10 ml PBS and 3 $\mu$l 30% $H_2O_2$) which produced an insoluble brown precipitate on the membrane for sample concentrations of human hepatitis B surface antigen (ad/ay) greater than 1 $\mu$g/ml. Similar results were obtained using a nitrocellulose membrane (BioRad; 0.45 micron).

EXAMPLE 3

The procedure of Examples 1 and 2 was repeated to test a sample for the presence of HIV p24 antigen and HIV antibody in a blood specimen. Four test sections were prepared on a membrane, one for the HIV antibody, one for the HIV p24 antigen, a positive control, and a negative control. The HIV antibody test section was prepared using p24 lysate (DuPont); the p24 antigen test section using mouse anti-p24 MAb (DuPont or Chemicon); and the positive control section using the mouse anti-p24 antibody which had been conjugated with a peroxidase enzyme system by the one-step glutaraldehyde method. Following blocking, the membrane was cut into sections each of which contained a test site. Each section was placed in a filter holder and developed as in the preceding examples. The HIV antibody test section was contacted with the mouse anti-p24 antibody and developed using goat antimouse $I_gG$ antibody conjugated with horseradish peroxidase (Jackson Laboratories) to yield a positive result for the presence of HIV antibody at concentrations of about 1 microgram/ml. The p24 test section was contacted with the p24 lysate and developed with the HPO-conjugated mouse anti-p24 MAb to yield positive results for the presence of the p24 antigen at a similar concentration. The positive control tested consistently positive, while the negative control tested consistently negative.

EXAMPLE 4

A dip-stick type device was utilized to determine the presence of human choriogonadotropin (hCG), an antigen present in the urine of pregnant women. A mouse-derived monoclonal antibody against hCG was covalently bound to a section of a nylon membrane (immunodyne immunosorb; 1 micron) as in Example 1. On another section membrane a polyclonal-alkaline phosphatase enzyme-conjugated rabbit-derived antibody against hCG was bound as a positive test control. Another membrane section was treated with blocking solution as a negative test control. Following this binding process, the entire membrane was blocked with phosphate-buffered saline (PBS) at pH 7.4 containing 0.05% TWEEN 20 and 0.19 M glycine and allowed to dry under vacuum at room temperature. A cotton matrix was prepared by cutting a cotton sheet (Schleicher & Schuell 903 specimen collection paper; basis wt. 110 lbs/ream; 0.5 mm caliper) into about 6 mm square sections onto which was placed 200 microliters of PBSTWEEN containing 1 microgram of enzyme-conjugated antibody (alkaline phosphatase-rabbit, anti-hCG), and dried in vacuum at room temperature. The membrane sections were then cut apart into about 6 mm square pieces and each inverted over the cotton squares. These were then sealed together on a glass slide by taping all edges. The membrane was wetted with a drop of sample containing hCG (from 0 to 2500 mIU/ml concentrations) which was allowed to absorb through the membrane for five minutes. The membrane was washed with several mls of barbital buffer at pH 9.6, and then the color developed by immersing the device in nitroblue tetrazolium. A black dot was visible (on the face-down side of the membrane) for the positive control and for all samples containing concentrations greater than 25 mIU/ml of hCG. The negative test membrane remained free of any color development. Similar results were obtained by washing with distilled water instead of barbital buffer.

EXAMPLE 5

A test similar to that of Example 4 was performed for human hepatitis B surface antigen. However, the primary antibody was a mouse monoclonal against hepatitis B surface antigen (ad/ay) and the secondary antibody was an equine polyclonal against hepatitis B surface antigen (ad/ay) conjugated with a peroxidase enzyme system as described in Example 2. The substrate for the peroxidase enzyme was similarly 3,3'-diaminobenzidine (DAB) as in Example 2 which produces an insoluble brown product. The procedure followed that for Example 4 and the presence of hepatitis B surface antigen could be visually detected at concentrations greater than 1 $\mu$g/ml.

EXAMPLE 6

The procedure of Example 4 was repeated using the reagents described in Example 3 with excellent results for the detection of HIV antibody and p24 antigen at similar concentrations with consistent positive and negative controls.

EXAMPLE 7

The procedures of Examples 4-6 are repeated except that a wafer is used instead of the cotton matrix. The wafer is formed on the glass slide by placing 200 microliters of 0.1% gelatin glycine-PBS solution containing 1 microgram of the conjugated antibody on the glass slide, and drying under vacuum at room temperature. Similar results are obtained.

EXAMPLE 8

Examples 3 and 6 are repeated except that non-cross-reactive labeled antibodies are contained in the same developing solution to simultaneously treat all test sections of the membrane. The labeled antibodies are obtained by partially digesting gel chromatography affinity-purified p24 viral lysate with trypsin. Fractions of the p24 digestion are collected by SDS gel electrophoresis and transblotting onto BioRad APT paper. The fractions are hybridized with BSA, mixed with Freund's complete adjuvant and used to immunize mice. Spleen cells harvested from the immunized mice are used to develop hybridoma cell lines. The cell lines are screened and a cell line is selected for antibodies which are specific for p24 antigen, but not specific for any of the epitopes contained in at least one of the p24 digestion fractions which also contains epitopes for wild-type HIV antibodies. This p24 digestion fraction is used a the membrane-coupled antigenic substance.

The foregoing description is merely exemplary and illustrative of the invention and many variations will occur to those of skill in the art in view thereof. It is intended that all such variations within the scope and spirit of the appended claims be embraced thereby.

I claim:

1. A serodiagnostic device comprising
   (A) a porous membrane that presents a first surface and an opposing second surface, wherein a first immunoreagent is bound to said second surface and is capable of binding a foreign analyte to form a complex when said foreign analyte is brought into contact with said first immunoreagent by exposing said first surface to a sample containing said foreign analyte;
   (B) a matrix that presents a first surface and an opposing second surface and that contains a second immunoreagent which is labeled and which is capable of binding said foreign analyte to form a labeled complex when said foreign analyte is sandwiched between said first immunoreagent and said second immunoreagent, wherein (i) said first surface of said matrix is adjacent to said second surface of said membrane, (ii) said matrix is wettable by or soluble in an aqueous fluid, and (iii) second immunoreagent is mobilized when said matrix is wetted; and
   (C) a support upon which said matrix and said membrane are provided such that said second surface of said matrix is adjacent to said support.

2. A serodiagnostic device according to claim 1, wherein each of said first and second immunoreagents comprises monoclonal or polyclonal antibody.

3. A serodiagnostic device according to claim 1, wherein said foreign analyte is selected from the group consisting of human choriogonadotropin, a hepatitis B surface antigen and a HIV-associated antigen.

4. A serodiagnostic device according to claim 1, wherein said foreign analyte is an HIV antibody.

5. A serodiagnostic device according to claim 4, wherein said HIV antibody is an anti-p24 antibody.

6. A serodiagnostic device according to claim 1, wherein each of said first and second immunoreagents is an antigen.

7. A serodiagnostic device according to claim 8, wherein said antigen is an HIV antigen.

8. A serodiagnostic device according To claim 7, wherein said HIV antigen is p24.

9. A serodiagnostic device according to claim 1, wherein said device comprises a plurality of test pads provided on said support and wherein at least a first test pad of said plurality is comprised of (i) a porous membrane that presents a first surface and an opposing second surface, wherein a first immunoreagent is bound to said second surface and is capable of binding a foreign analyte to form a complex when said foreign analyte is brought into contact with said first immunoreagent by exposing said first surface to a sample containing said foreign analyte; (ii) a matrix that presents a first surface and an opposing second surface and that contains a second immunoreagent which is labeled and which is capable of binding said foreign analyte to form a labeled complex when said foreign analyte is sandwiched between said first immunoreagent and said second immunoreagent, wherein (a) said first surface of said matrix is adjacent to said second surface of said membrane, (b) said matrix is wettable by or soluble in an aqueous fluid, and (c) second immunoreagent is mobilized when said matrix is wetted.

10. A serodiagnostic device according to claim 9, wherein at least one other test pad of said plurality provides a positive or negative control relative to said first test pad.

11. A serodiagnostic device according to claim 1, wherein said second immunoreagent is labeled with an enzyme.

12. A method for serodiagnosis of a fluid sample, comprising the steps of
    (A) inserting a serodiagnostic device according to claim 1 into a sample of test fluid containing said foreign analyte such that said sample contacts said membrane, whereby said foreign analyte (i) traverses said first surface of said membrane to said second surface of said membrane and binds said first immunoreagent and (ii) mobilizes said second immunoreagent; then
    (B) inserting said serodiagnostic device into a washing solution such that said solution contacts said membrane, whereby said second immunoreagent not bound to said complex is removed from said matrix; and thereafter
    (C) inserting said serodiagnostic device into a solution of a compound that reacts with said labeled complex to produce a detectable reaction product.

13. A method according to claim 12, wherein said serodiagnostic device comprises a plurality of test pads provided on said support and wherein at least one test pad of said plurality is comprised of (i) a porous membrane that presents a first surface and an opposing second surface, wherein a first immunoreagent is bound to said second surface and is capable of binding a foreign analyte to form a complex when said foreign analyte is brought into contact with said first immunoreagent by exposing said first surface to a sample containing said foreign analyte; (ii) a matrix that presents a first surface and an opposing second surface and that contains a second immunoreagent which is labeled and which is capable of binding said foreign analyte to form a labeled complex when said foreign analyte is sandwiched between firs immunoreagent and said second immunoreagent, wherein (a) said first surface of said matrix is adjacent to said second surface of said membrane, (b) said matrix is wettable or by soluble in an aqueous fluid, and (c) second immunoreagent is mobilized when said matrix is wetted.

14. A method according to claim 13, wherein said reaction product is detectable by visual observation of said serodiagnostic device after step (C).

15. A method according to claim 12, wherein said test fluid is human urine.

16. A method according to claim 12, wherein said test fluid is human serum or whole blood.

17. A method according to claim 12, wherein said reaction product indicates the presence of human choriogonadotropin, a hepatitis B surface antigen or a HIV-associated antigen.

18. A method according to claim 17, wherein said reaction product indicates the presence of p24 antigen.

19. A method according to claim 12, wherein said reaction product indicates the presence of an HIV antibody.

20. A method according to claim 19, wherein said HIV antibody is anti-p24 antibody.

* * * * *